United States Patent [19]
Deutsch

[11] Patent Number: 5,097,828
[45] Date of Patent: Mar. 24, 1992

[54] THERMOELECTRIC THERAPY DEVICE

[76] Inventor: Richard Deutsch, 8 Mayview Ave., Islip, N.Y. 11751

[21] Appl. No.: 587,407

[22] Filed: Sep. 25, 1990

[51] Int. Cl.⁵ .............................................. A61F 7/00
[52] U.S. Cl. .................................................. 128/399
[58] Field of Search ............... 128/399, 24.1, 34, 800, 128/801; 606/30

[56] References Cited

U.S. PATENT DOCUMENTS

| | | | |
|---|---|---|---|
| 1,480,353 | 1/1924 | Wappler | 128/800 |
| 1,653,901 | 12/1927 | Haessly | 128/399 |
| 1,844,247 | 2/1932 | Freemon | 128/399 |
| 3,133,539 | 5/1964 | Eidus | 128/399 |
| 3,168,895 | 2/1965 | Okuhara | 128/399 |
| 3,207,159 | 9/1965 | Tateisi | 128/399 |
| 3,424,165 | 1/1969 | Moss | 128/801 |
| 3,533,397 | 10/1970 | Scher | 128/399 |
| 4,308,012 | 2/1981 | Tamler et al. | 128/741 |
| 4,585,002 | 4/1986 | Kissin | 128/399 |
| 4,607,624 | 8/1986 | Jefferson | 128/399 |
| 4,640,284 | 2/1987 | Ruderian | 128/399 |
| 4,676,246 | 1/1987 | Korenaga | 128/399 |
| 4,722,326 | 2/1988 | Ruderian | 128/24.1 |
| 4,741,338 | 5/1988 | Miyamae | 128/399 |
| 4,860,748 | 8/1989 | Chiurco et al. | 128/399 |
| 4,878,493 | 11/1989 | Pasternak et al. | 128/801 |
| 4,915,108 | 4/1990 | Sun | 128/399 |

FOREIGN PATENT DOCUMENTS 2191669 12/1987 United Kingdom ............... 128/399

Primary Examiner—William H. Grieb
Attorney, Agent, or Firm—Hoffmann & Baron

[57] ABSTRACT

A therapeutic device is provided for heating or cooling the skin and underlying body tissue. The device includes a handle and a thermally conductive head secured to the handle. The head includes a thermally conductive contact plate which is thermally isolated from the head. One or more Peltier effect devices are provided for heating or cooling the contact plate depending upon the polarity of the current. The head and handle function as a heat sink for dissipating heat generated by the Peltier effect devices. A fan is also provided within the head for heat dissipation purposes. A bag or pouch filled with a thermally conductive fluid may be mounted to the head and positioned adjacent to the contact plate. The bag or pouch conforms to the surface of the body to which it is applied. A porous bag may be employed if moist heat is desired. The contact plate may be connected to a high voltage source if electrical stimulation is desired.

22 Claims, 4 Drawing Sheets

THERMOELECTRIC THERAPY DEVICE

BACKGROUND OF THE INVENTION

1. Field of the invention.

The field of the invention relates to devices for heating and/or cooling the surface of the body.

2 Brief description of the prior art.

The use of heat and cold for therapeutic purposes is well known. Hot water bags, ice packs, and the like have commonly been used to alleviate pain, to stimulate the flow of blood, or to restrict the flow of blood beneath the surface of the skin. One of the problems with hot water bags is that the temperature steadily decreases during use, thereby necessitating refilling them with a heated liquid. Ice packs steadily increase in temperature when applied to the skin, and ice must accordingly be added from time to time if a cold temperature is to be maintained. It is also difficult to regulate the temperature of an ice pack or a hot water bottle such that it is neither too cold nor too hot when applied to the skin.

A number of therapeutic devices have been developed which employ Peltier thermoelectric units for providing heat or cold. Such devices include switches which allow reversing the polarity of the current passing through the thermoelectric units, thereby determining whether a hot or a cold stimulus is to be applied thereby. U.S. Pat. No. 3,207,159 discloses such a device which includes a probe for heating or cooling selected cutaneous points. U.S. Pat. Nos. 4,585,002 and 4,860,748 disclose devices which employ microprocessors for controlling the duration and/or intensity of heat and cold generated by Peltier thermoelectric units. U.S. Pat. Nos. 3,133,539, 3,168,895, 4,640,284 and 4,915,108 disclose various other therapeutic devices for applying heat or cold to the skin.

SUMMARY OF THE INVENTION

It is an object of the invention to provide a therapeutic device for applying heat or cold to the skin and underlying muscles.

It is another object of the invention to provide a device which can apply heat or cold to the skin and underlying muscles in a controlled manner.

A still further object of the invention is to provide a device for massaging the skin and underlying muscles while applying heat or cold thereto.

A still further object of the invention is to provide a device which electrically stimulates the skin and underlying muscles while applying heat or cold thereto.

In accordance with these and other objects of the invention, a therapeutic device is provided which includes a handle, a thermally conductive head secured to the handle, and a thermally conductive member secured to the front end of the head. Thermoelectric means are provided for heating or cooling the thermally conductive member. The head includes a thermally conductive portion adjoining the thermoelectric means such that the head can function as a heat sink. The handle also is preferably thermally conductive so that it too can dissipate heat. A fan is provided for creating air turbulence within the head.

The device is preferably battery powered, the handle defining a chamber in which one or more batteries can be inserted. A controller board may be connected to a switch within the handle, the switch being connected to the battery. A high voltage source may be connected between the switch and thermally conductive member so that electrical stimulation may be provided to the skin.

The thermally conductive member can be a hard or soft plate-like member. If a soft, resilient, thermally conductive member is employed, it may be provided as an assembly which is detachable from the front end of the head.

DETAILED DESCRIPTION OF THE INVENTION

Figure 1:
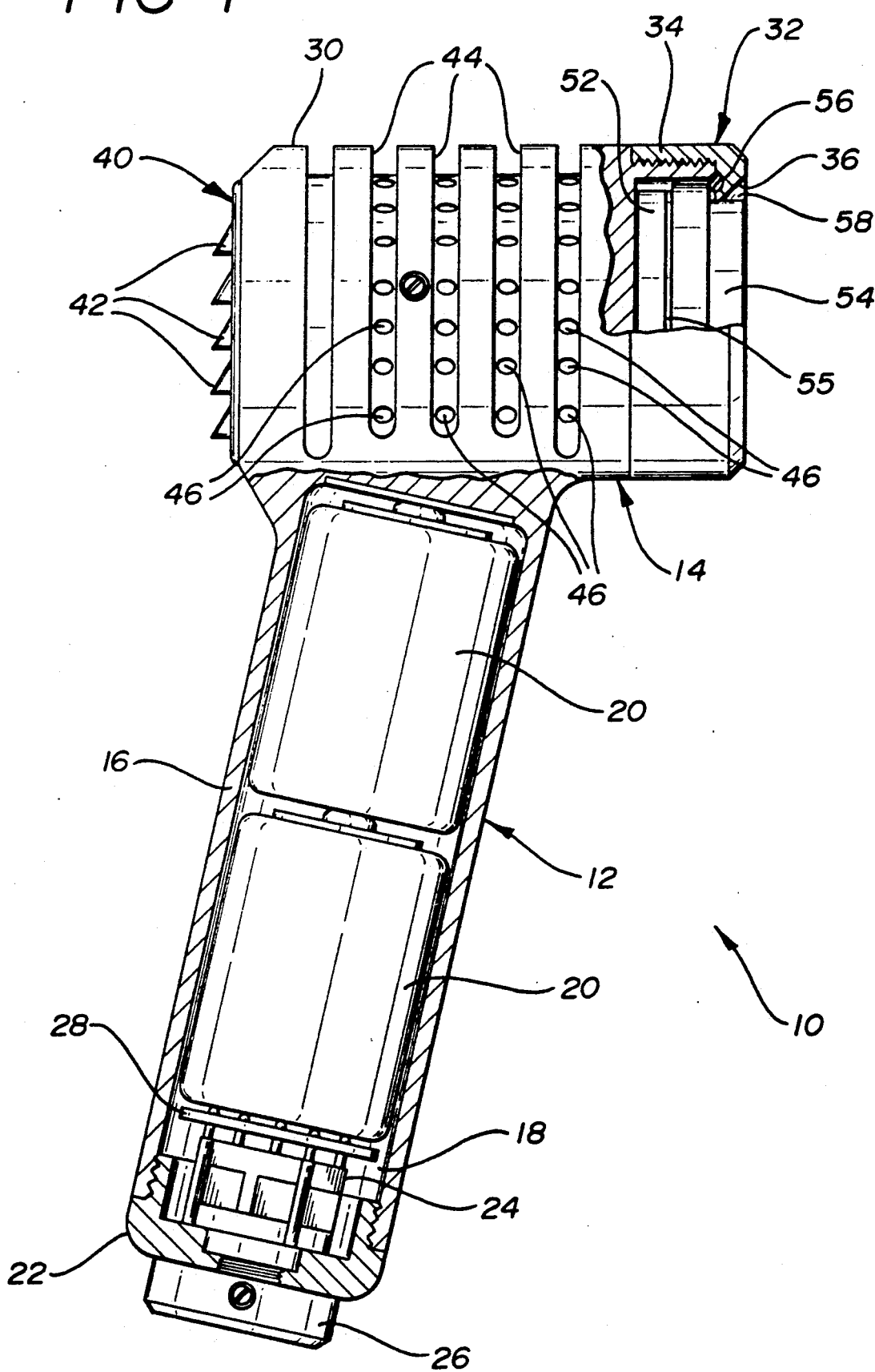
FIG. 1 is a partially sectional, elevation view of a thermoelectric therapy device in accordance with the invention.

A therapy device 10 as shown in FIG. 1 is provided. The device includes a substantially cylindrical handle 12 and a substantially cylindrical head 14. The handle and head are preferably of integral construction, and are made from a thermally conductive material such as aluminum, copper, or an alloy containing both of these metals and silicon.

The handle includes a cylindrical wall 16 which defines an enclosure 18. The enclosure is adapted for receiving at least one battery. Two rechargeable, nickel-cadmium batteries 20 are positioned within the enclosure shown in FIG. 1. Other types of batteries may alternatively be employed.

A tail cap 22 is threadably secured to the end of the handle 12 opposite from the head 14. A three-way switch 24 is positioned within the enclosure 18 and adjacent to the tail cap. A knob 26 extending outside the tail cap controls the operation of the switch. The opposite end of the switch is connected to a controller board 28.

Figure 2:
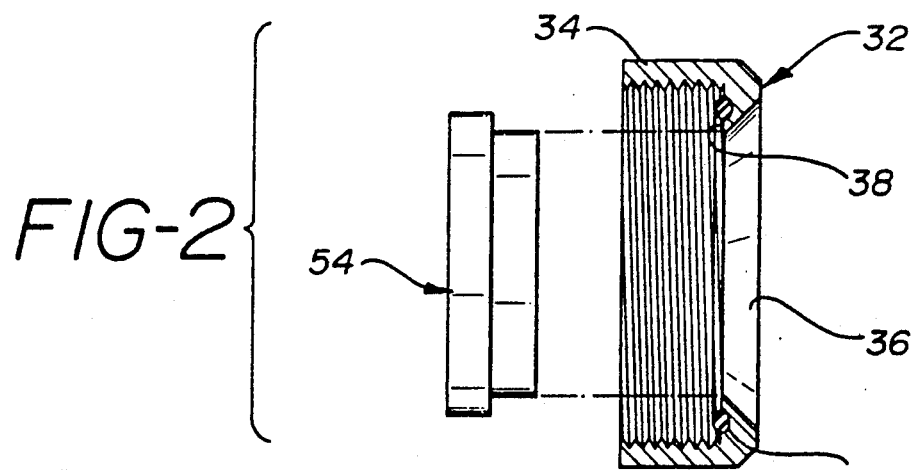
FIG. 2 is an exploded, side elevation view of a face cap and contact plate used within the device.
Figure 3:
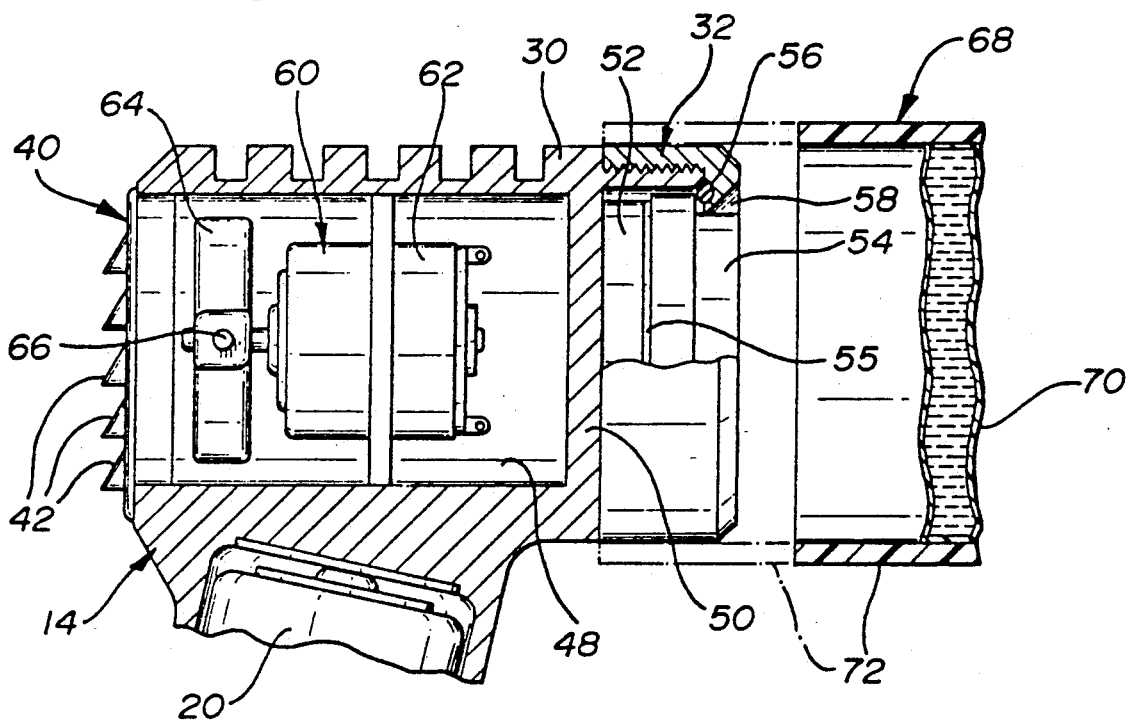
FIG. 3 is a sectional, elevation view of the head of the device.

Referring now to FIGS. 1-3, the head 14 includes a substantially cylindrical wall 30 having an opening at its front end and an opening at its rear end. A face cap 32 is threadably secured to the front end of the head. The face cap includes an annular body 34 having a bevelled front wall 36. A shoulder 38 is defined by the rear surface of the front wall, as best shown in FIG. 2.

A vented plate 40 including fins 42 is secured to the rear end of the head. A plurality of grooves 44 are defined in the outer surface of the cylindrical wall 30. The grooves 44 extend circumferentially about the axis of the head. Alternatively, the grooves may extend axially. Vent openings 46 extend through the cylindrical wall 30 at the grooved portions thereof.

The cylindrical wall 30 defines a chamber 48. The vented plate 40 defines one end of the chamber while a front wall 50 defines the opposite end thereof. A thermo module 52 adjoins the front side of the front wall. The thermo module includes thermoelectric means including a Peltier effect device. A hat-shaped, thermally conductive contact plate 54 adjoins the thermo module. A thin, ceramic insulator 55 is positioned between the thermo module 52 and contact plate 54, thereby electrically insulating the latter. The contact plate is thermally isolated from the face cap 32, which maintains it in position, by an O-ring 56. The face cap may alternatively be made from plastic to provide such thermal insulation. An annular space 58 defined between the inner surface of the end cap and the edge of the contact plate also provides thermal isolation. The O-ring is slightly compressed between the shoulder 38 of the face cap and a shoulder defined by the hat-shaped contact plate. The contact plate accordingly does not tend to move axially or laterally with respect to the head 14.

A fan 60 is mounted within the chamber 48, as shown in FIG. 3. Other equivalent means for circulating air could alternatively be employed. The fan includes a motor 62 having a blade 64 secured thereto. The blade is positioned adjacent to the vented plate 40. A weight 66 may be added to one of the fan blades to cause the head to vibrate slightly when the fan is operated.

A fluid-filled, thermally conductive end piece 68 may be mounted to the front end of the head 14 as shown in dotted lines in FIG. 3. The end piece includes a fluid-filled bag 70 secured to an elastic sleeve 72. The fluid-filled bag conforms to the surface of the skin to which it is applied. It is either heated or cooled depending upon the temperature of the adjoining contact plate.

Figure 6:
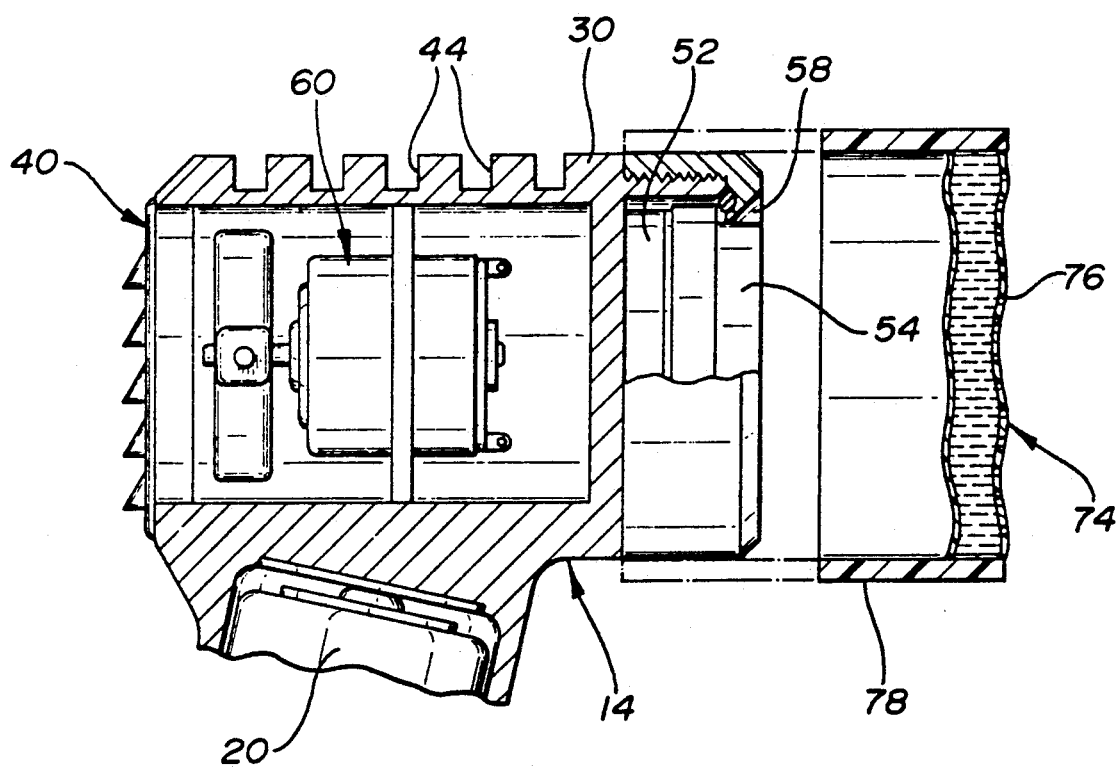
FIG. 6 is a sectional view of a porous pouch secured to the front end of the head of the device.

In an alternative embodiment of the invention shown in FIG. 6, a fluid-filled bag 74 having a porous wall 76 is secured to the front end of the head by an elastic sleeve 78. Moist heat may be accordingly provided by the device 10 when fitted with such a bag.

Figure 4:
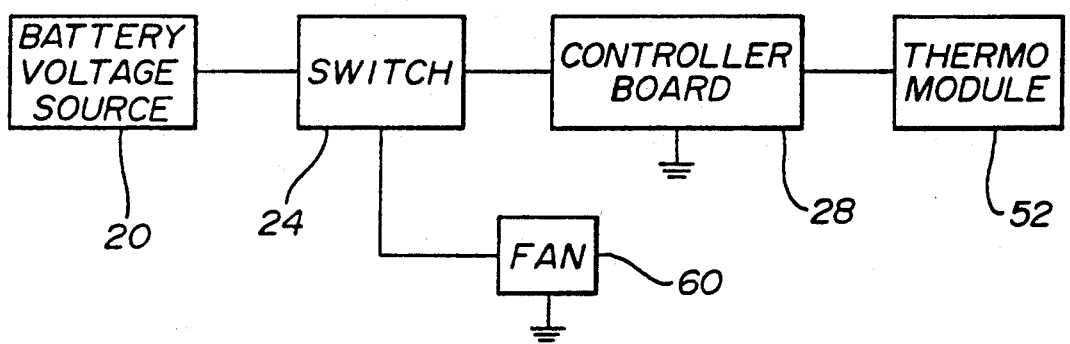
FIG. 4 is a schematical illustration of the electrical circuit employed within the device.
Figure 5:
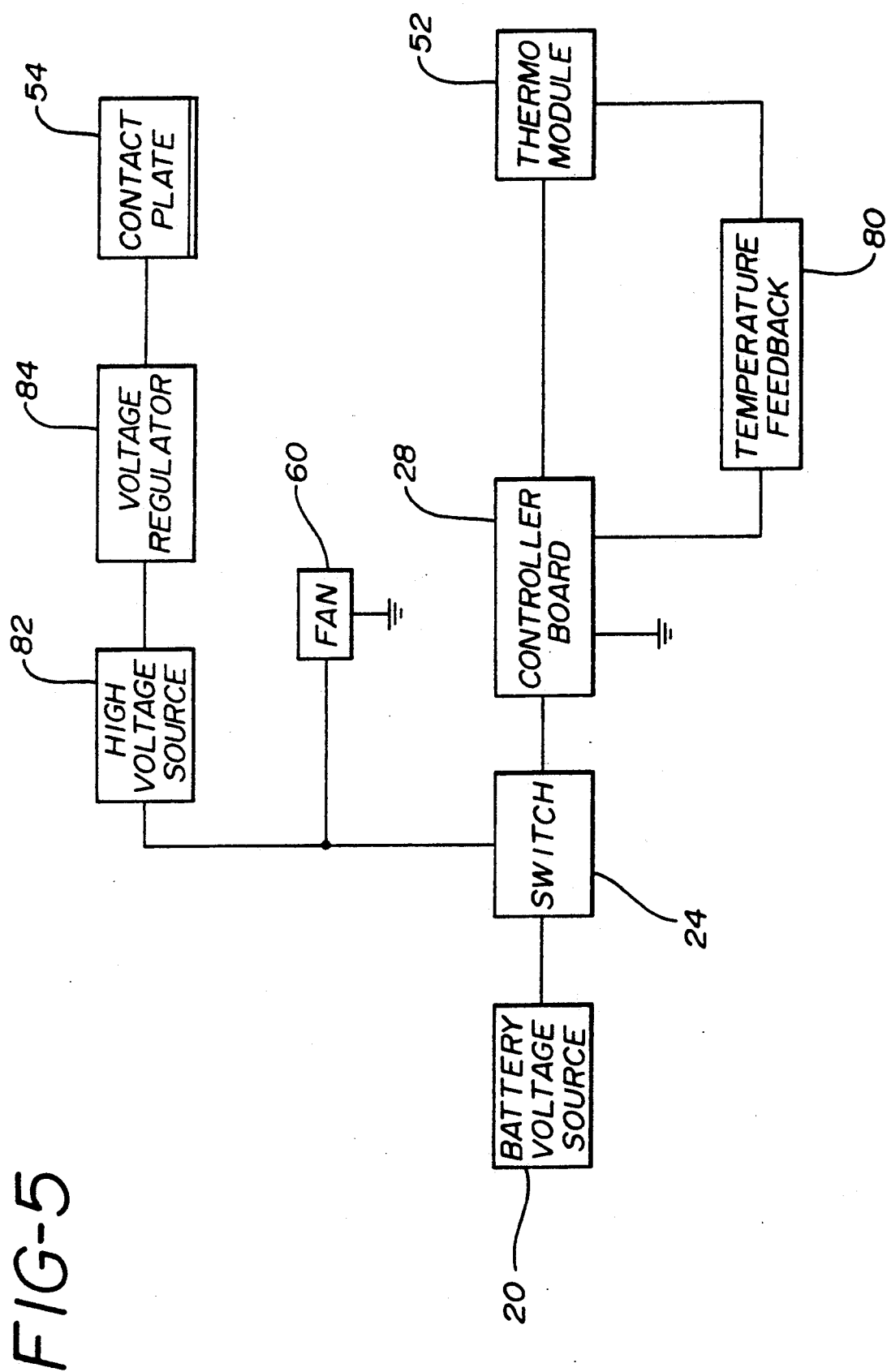
FIG. 5 is a schematical illustration of an alternative electrical circuit employed within the device.

FIG. 4 provides a schematical illustration of one electrical circuit which may be used within the device 10. An alternative circuit is shown in FIG. 5. This circuit includes the same elements shown in FIG. 4, plus a temperature feedback loop 80, a high voltage source 82, and a voltage regulator 84. The temperature feedback loop allows the temperature of the thermo module, and therefore the contact plate, to be maintained within preselected limits. In addition, the temperature may be varied as a function of time between hot and cold.

Electrical stimulation of the skin and underlying muscles may be provided through the use of the high voltage source and the voltage regulator. The high voltage source may be a multivibratory transformer circuit or the like. A polarity switch (not shown) may also be employed in this loop. The switch controls the direction of the current and, therefore, the type of electrical therapy provided (i.e. desensitization (sedation) or stimulation (tetenization)).

In operation, the device is used for applying heat or cold to a relatively large, circular area defined by the outer surface of the contact plate 54. The knob 26 is turned to actuate the switch 24. Current flows in a selected direction through the thermo module 52, thereby causing it to heat or cool the contact plate 54. The fan is simultaneously actuated, and helps maintain the thermal gradient across the thermo module and the device itself.

The relative surface areas and masses of the thermo module, contact plate, head 14 and handle 12 are such that excess heat which may be generated by the thermo module is easily absorbed by the head and handle. The head and handle, each being thermally conductive and having much larger masses and surface areas than the contact plate, function as a large heat sink which easily dissipates such heat. The fan, grooves and vent openings are also strategically positioned to efficiently circulate and exhaust air within the chamber 48. There is accordingly no danger of thermal runaway regardless of how long the device is operated.

The knob 26 is turned to a different position if one desires to reverse the current flow through the thermo module. The fan is actuated regardless of the direction of current flow through the thermo module.

If one desires to apply moist heat to the skin, a porous pouch or bag may be mounted to the front end of the head as shown in FIG. 6. The size of the pores is exaggerated in this figure for illustrative purposes. Liquid within the pouch can slowly escape as the pouch is applied to the skin. The knob 26 is turned in the appropriate direction so that heat is applied to the contact plate and, in turn, the bag 74.

A leak-proof bag 70 is used if no moisture is necessary or desired. Such a bag can be mounted to the head 14 prior to providing current to the thermo module. A thermally conductive, gel-like substance may be provided within the bag. The bag readily conforms to the body surface to which it is applied.

A gentle vibratory motion is imparted by the device 10 due to the eccentric weighting of the fan blade 64. Such vibration can alternatively be provided by a mechanical vibrator.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A therapeutic device for heating or cooling the skin and underlying muscles, comprising:
   a handle having an exposed outer wall made from a thermally conductive material;
   a thermally conductive head secured to said handle such that heat is readily transferable from said head to said handle, said head including a front end and a rear end;
   a thermally conductive contact plate secured to said front end of said head;
   means for thermally and electrically isolating said contact plate from said head;
   thermoelectric means adjoining said contact plate, said thermoelectric means being capable of producing a temperature change in said contact plate in response to an electrical current flowing therethrough;
   means for causing current to flow through said thermoelectric means in a first direction, thereby causing said thermoelectric means to heat said contact plate;
   means for causing current to flow through said thermoelectric means in a second direction, thereby causing said thermoelectric means to cool said contact plate;
   said head including a thermally conductive portion adjoining said thermoelectric means such that said head can function as a heat sink for dissipating heat generated by said thermoelectric means;
   a fan positioned within said head; and
   a plurality of vent openings extending into said head.

2. A device as described in claim 1 wherein said thermoelectric means include a Peltier effect device.

3. A device as described in claim 2 wherein said handle includes a chamber for receiving at least one battery, said fan and said Peltier effect device being electrically connected to said at least one battery.

4. A device as described in claim 3 wherein said head includes a front wall adjoining said Peltier effect device, said front wall being in opposing relation to said fan.

5. A device as described in claim 4 wherein said head includes a substantially cylindrical wall defining a chamber, said front wall including an inner surface defining a front end of said chamber, said handle having an elongate configuration and extending at an angle from said head.

6. A device as described in claim 5 wherein said head includes a vented rear wall defining the rear end of said head, said fan being positioned between said front wall and said rear wall.

7. A device as described in claim 6 wherein said head includes a plurality of grooves extending into the outer surface of said substantially cylindrical wall.

8. A device as described in claim 7 wherein said grooves extend substantially circumferentially about the longitudinal axis of said substantially cylindrical wall, at least some of said vent openings located in said grooves and establishing fluid communication between said chamber and the atmosphere.

9. A device as described in claim 5 including a face cap threadably secured to the front end of said head, said means for thermally and electrically isolating said contact plate being positioned between an inner surface of said end cap and an outer surface of said contact plate.

10. A device as claimed in claim 9 wherein said means for thermally and electrically isolating said contact plate includes a O-ring made from a thermally and electrically non-conductive material.

11. A device as described in claim 1 including a fluid-filled bag mounted to the front end of said head, said fluid-filled bag including a porous wall in opposing relation to said contact plate through which moisture may penetrate.

12. A device as described in claim 11 wherein said bag is detachably secured to the front end of said head.

13. A device as described in claim 1 including a voltage source electrically connected to said contact plate, whereby said contact plate is capable of providing electrical stimulation to the skin.

14. A device as described in claim 1 including vibration means positioned within said head for vibrating at least a portion of said head.

15. A device as described in claim 1 wherein said handle has a generally cylindrical, elongate configuration and extends at an angle from said head.

16. A therapeutic device for heating or cooling the skin and underlying muscles, comprising:

a thermally conductive, elongate handle having an exposed, thermally conductive outer wall and defining an enclosure adapted for receiving a battery;

a thermally conductive head secured to and extending at an angle with respect to said handle, said head including a front end and a rear end and a chamber defined therein;

a thermally conductive contact member secured to the front end of said head;

thermoelectric means positioned within said head, said thermoelectric means being capable of heating or cooling said contact member depending upon the polarity of an electrical current flowing therethrough;

said head and said handle being positioned with respect to said thermoelectric means such that heat is readily transferrable from said thermoelectric means to said head and handle;

fan means for causing air turbulence within said chamber; and a vent opening for exhausting air from said chamber.

17. A device as described in claim 16 wherein said contact member is a plate including a substantially circular front surface.

18. A device as described in claim 16 wherein said contact member is a resilient, thermally conductive pad.

19. A device as described in claim 16 including a porous bag mounted to the front end of said head, said porous bag including a fluid-filled chamber positioned adjacent to said contact member, a porous wall adjoining said chamber, and means for releasably securing said bag to the front end of said head.

20. A hand-held therapeutic device for treating the skin, comprising:

a housing including a contact plate;

thermoelectric means adjoining said contact plate for producing a temperature change in said contact plate in response to an electrical current flowing therethrough; and a fluid-filled bag secured to said housing adjacent to said thermoelectric means, said fluid-filled bag including a porous exterior wall which may be applied against the skin for providing moisture to the skin.

21. A device as described in claim 20 including means for releasably securing said fluid-filled bag to said housing.

22. A device as described in claim 21 wherein said means for releasably securing said fluid-filled bag to said housing includes a sleeve extending over a portion of said housing and a fluid-containing enclosure secured to said sleeve.

* * * * *